United States Patent

Albrektsson et al.

[11] Patent Number: 5,702,473
[45] Date of Patent: Dec. 30, 1997

[54] CUP

[75] Inventors: Björn Albrektsson, Onsala; Lars Carlsson, Kullavik; Magnus Jacobsson, Göteborg; Tord Röstlund, Kullavik; Stig Wennberg, Angered, all of Sweden

[73] Assignee: Astra Aktiebolag, Sodertalje, Sweden

[21] Appl. No.: 416,879

[22] PCT Filed: Dec. 21, 1994

[86] PCT No.: PCT/SE94/01233

§ 371 Date: Apr. 19, 1995

§ 102(e) Date: Apr. 19, 1995

[87] PCT Pub. No.: WO95/17140

PCT Pub. Date: Jun. 29, 1995

[30] Foreign Application Priority Data

Dec. 23, 1993 [SE] Sweden ............... 9304281

[51] Int. Cl.$^6$ .................................. A61B 2/32
[52] U.S. Cl. ............................ 623/22; 623/18
[58] Field of Search ............... 623/16, 18, 19, 623/22, 23

[56] References Cited

U.S. PATENT DOCUMENTS

| 4,145,764 | 3/1979 | Suzuki et al. | 623/16 |
| 4,164,794 | 8/1979 | Spector et al. | |
| 4,795,469 | 1/1989 | Oh | 623/22 |
| 4,813,959 | 3/1989 | Cremascoli | 623/23 |
| 4,871,368 | 10/1989 | Wagner | 623/22 |
| 4,883,491 | 11/1989 | Mallory et al. | 623/22 |
| 4,963,154 | 10/1990 | Anapliotis et al. | 623/22 |
| 4,997,447 | 3/1991 | Shelley | 623/22 |
| 5,108,446 | 4/1992 | Wagner et al. | 623/22 |
| 5,263,986 | 11/1993 | Noiles et al. | 623/22 |

FOREIGN PATENT DOCUMENTS

| A2575102 | 12/1993 | European Pat. Off. | |
| 2558446 | 7/1976 | Germany | 623/22 |
| 2645101 | 4/1978 | Germany . | |
| 3101333 | 12/1981 | Germany . | |
| 3322978 | 1/1985 | Germany . | |
| 3602081 | 10/1986 | Germany | 623/22 |

Primary Examiner—David Isabella
Attorney, Agent, or Firm—White & Case

[57] ABSTRACT

The invention relates to a cup-shaped member for a hip joint prosthesis, for implantation into a cavity in the bone tissue in the acetabulum, comprising an acetabular cup (1) made of metal a ceramic material or any other suitable material, preferably of titanium, the outside of said cup being rotationally symmetrical around a central axis of symmetry. The outer side of the cup (1), that is the side which is to face the bone tissue, is provided with at least one circumferential bead (5) close to the edge of the cup (1), said bead (5) having a barb-like shape in section and consequently allowing the cup (1) to be pushed into said cavity but counter-acting the removal of said cup (1) from said cavity, said outer side including said bead(s) (5) being provided with a rough structure serving as a file when said cup (1) is moved or rotated in said cavity.

5 Claims, 1 Drawing Sheet

CUP

TECHNICAL FIELD OF THE INVENTION

The present invention relates to a cup-shaped member for a hip joint prosthesis for implantation into a cavity in the bone tissue in the acetabulum. The cup-shaped member comprises an acetabular cup made of metal, a ceramic or any other suitable material, preferably of titanium. The exterior shape of the cup-shaped member is rotationally symmetrical around a central axis of symmetry.

BACKGROUND TO THE INVENTION

Artificial hip joints have been used and implanted into humans for a long period of time. The joints normally comprise one femoral part which is intended to be inserted or implanted into the femur and which carries a ball-shaped articulation element, normally made of metal or a ceramic material. The joint further normally comprises a cup-shaped member, i.e., an acetabular cup, which is to be inserted into or attached to the acetabulum, and which is to hold a complementary, cup-shaped liner, normally made of Ultra High Molecular Weight Polyethylene (UHMWPE) or a similar polymer material, in which the ball-shaped element is to articulate or rotate.

The depth of the bone tissue which is available in the acetabulum for attaching the acetabular cup is limited in most directions. The acetabular cup per se is furthermore rather flat and shallow, which means that the cup at least to some extent may be considered to be more or less placed directly onto the surface of the bone tissue and not into the bone tissue, this in contrast to most other commonly used bone implants, such as screw-shaped dental implants or standard femoral implants. These factors make it difficult to design an acetabular cup that easily will be attached to the bone tissue by means of the shape of the cup or to design efficient attachment means for the cup.

Some prior art acetabular cups are disclosed in for instance DE-A-24 54 635, DE-A-26 45 101, U.S. Pat. Nos. 3,903,549 and 4,795,470.

A metal which is commonly used in bone implants is titanium because of its proven affinity with bone tissue and its good biocompability. One particular property of titanium is its tendency to form a close connection with bone tissue. The formation of this close connection is often termed "osseointegration". One factor which may be important for a proper ossseointegration process is a relatively good fit between implant and bone tissue. Another important factor that will affect the degree relative immobility between implant and bone tissue.

The object of the present invention is to provide an acetabular cup which provides conditions favourable to the osseointegration process by influencing the factors described above and to provide a cup which will be firmly attached to the bone tissue.

BRIEF DESCRIPTION OF THE INVENTION CONCEPT

This object is achieved in that the outer side of the cup, that is the side which is to face the bone tissue, is provided with at least one circumferentially oriented bead close to the edge of the cup-shaped element, said bead having a barb-like shape in section and consequently allowing the cup-shaped element to be pushed into said cavity but counter-acting the removal of said cup-shaped element from said cavity, said outer side including said bead(s) being provided with a rough structure serving as a file or saw when said cup is pushed and/or rotated into said cavity.

Further advantageous embodiments are set forth in the dependent claims.

DETAILED DESCRIPTION OF A PREFERRED EMBODIMENT OF THE INVENTION

Figure 1:
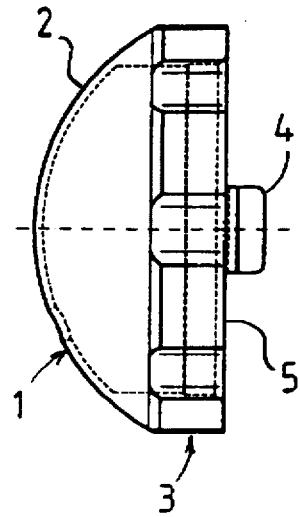
FIG. 1 shows a side view of an acetabular cup according to the invention
Figure 2:
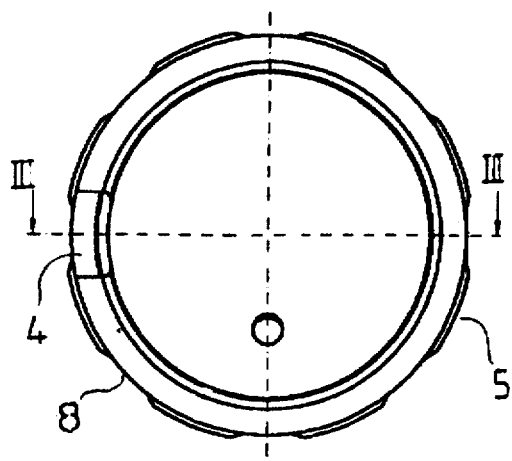
FIG. 2 shows a view of the cup of FIG. 1
Figure 3:
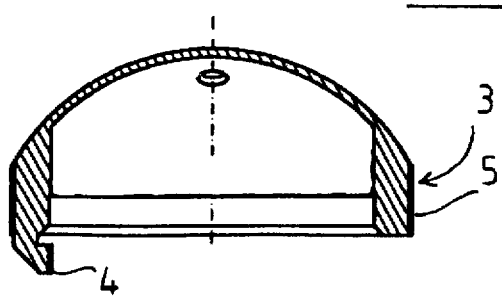
FIG. 3 a section along the line III—III in FIG. 2.
Figure 4:
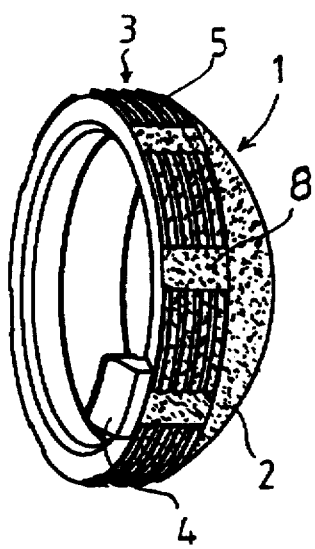
FIG. 4 shows a perspective view of the cup.
Figure 5:
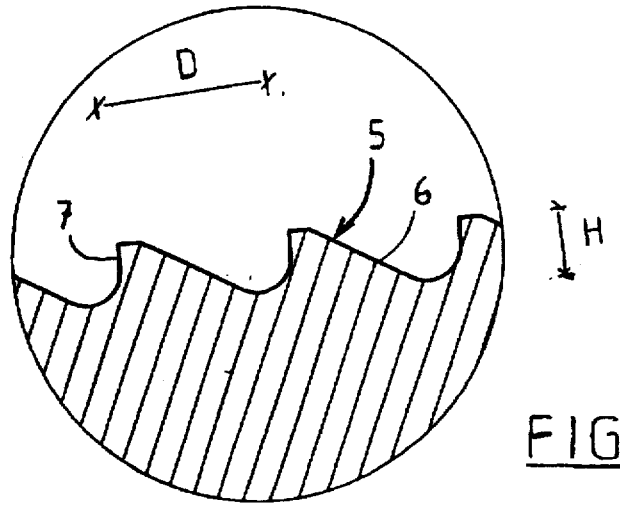
FIG. 5 details of the thread.

In this preferred embodiment the cup-shaped member comprises an acetabular cup 1 which is shown in detail in FIGS. 1–3. The cup 1 is intended to hold a complementary liner which may be attached to the cup according to any standard procedure or by any standard means.

The cup comprises two main parts, one spherical segment 2 and a cylindrical part 3 adjoining the edge of the spherical segment. The outside of the cylindrical part 3 is provided with a circumferential bead which is in the form of a thread 5. The forward side or flank 6 of the thread 5 forms an acute angle with the surface of the cylindrical part of the cup, i.e., the longitudinal orientation thereof, whereas the backward edge or flank 7 is more or less perpendicular to said surface of the cup. The pitch D of the thread may be about 2 mm and the height H about 1 mm in a normal sized cup. In this way the thread in section will have the shape of a barb or a saw tooth. When the cup is pushed into a cavity in the bone tissue, the thread consequently will allow the cup to be moved into the cavity but will prevent the cup to be moved out from the cavity.

The threads do not have to run around the entire periphery of the cylindrical part 3 and may for instance be broken by means of axial gaps 8 spaced equidistantly around the periphery.

The entire outer surface of the cup, including the cylindrical part 3 and the threads 5, is roughened. The rough structure should have relatively sharp edges so as to be able to function in a manner similar to a file. A suitable way of obtaining this roughness is by blasting the surface with $Al_2O_3$ having a particle size of about 0,25 mm at a pressure of 3–6 bar. It is also conceivable to use particles of $TiO_2$.

The free edge of the cylindrical part is also provided with a projecting lug 4, which may be used to lock the liner against rotation in the cup when the hip joint prosthesis actually is in use and the above-mentioned ball-shaped member on the femoral part of the prosthesis moves in the liner.

When the cup is to be mounted, a cavity is cut in the bone tissue in the acetabulum. The shape of this cavity corresponds closely to the outer surface of the cup apart from the threads. The diameter of the cavity preferably is about 1 mm smaller than the diameter of the core part of the cylindrical part of the cup, i.e. about 1 mm smaller than the diameter as measured from the tips of the threads 5. The cup is then gently tapped as far into the cavity as possible. The cup will now be held in the cavity by means of the threads, which will be pressed into the walls of the cavity. The inward movement of the cup in the cavity will result in that the roughness on the exterior of the cup will act as a file, to some extent shaping the cavity after the shape of the cup. Some scraped-off bone tissue will also be deposited into the roughness.

The cup now may be turned, for instance a quarter of a turn in the cavity by means of a tool engaging the lug 4. This rotation of the cup has four important aspects, which are important individually and which are most advantageous in combination.

The first aspect is that the rough structure on the surface will act as a file on the inner surface of the cavity and thereby, if necessary, shape the cavity to conform exactly to the shape of the cup.

The second aspect is that the thread, which also will act as a file, will cut an inner thread on the inner surface of the cavity, by which means the cup will be held still more securely. The scraped-off bone tissue will be collected in the irregularities on the surface in both these cases.

The third aspect is that the cup will be screwed inwards into the cavity by means of the threads which are being cut, which means that the cup will be pressed inwards against the surface of the cavity.

The fourth aspect is that, as mentioned above, the irregularities on the surface will be filled with scraped off bone tissue which will promote the growth of newly formed bone tissue into the irregularities.

The cylindrical part of the cup will tend to stabilize the cup in the cavity since it will counteract any tendencies of the cup to rotate out of the cavity by a lateral sliding movement along the respective spherical surfaces of cup and cavity. The cylindrical part will also offer a larger attachment area along the edge of the cup, i.e., that part at which the forces from the bone tissue being a result from the fact that the cup is forced into the cavity are oriented perpendicularly relative to the axis of symmetry of the cup.

The threads on the exterior of the cylindrical part of the cup have the advantage that the cup easily may be unscrewed without damaging the cavity in the acetabulum, should the cup happen to be canted during the insertion process.

The invention of course can be varied in many ways within the scope of the appended claims. It should for instance be noted that the beads or threads do not have to be unbroken around the entire periphery of the cup and may for instance be in the form of one or several series of relatively short sections.

The roughness on the outer surface of the cup of course can be obtained in any suitable way resulting in relatively sharp-edged irregularities. Alternative methods might for instance be etching, mechanical scoring or cutting and possibly plasmaspraying. The roughness on the surface also could be obtained by providing the surface with a rough layer of some other material than the material in the cup, such as a plasmaprayed layer of hydroxy-apatite. The additional layer advantageously might be an osseointegration promoting or growth-stimulating material. The rough surface also could be provided with a thin layer of, or be treated with, a growth-stimulating agent.

The cup of course also can be provided witn additional fastening means, such as holes for bone screws, should the prevailing conditions be such as to require this.

The cup can be provided with other suitable tool-engaging means for the rotation of the cup than the lug described in the preferred embodiment. It should also be noted that the quarter turn of the cup described in connection with the preferred embodiment is only given as an example and that other rotation angles are possible.

We claim:

1. An acetabular cup for being implanted into a cavity in the bone tissue in the acetabulum as part of a hip joint prosthesis, the cup comprising:

a first part having an exterior surface in the shape of a spherical segment, the first part having an edge and the spherical segment having a first diameter at said edge;

a second part adjoining the first part at the edge, the second part having a cylindrical exterior surface for engagement with said cavity, said cylindrical exterior surface having a second diameter not greater than said first diameter of the spherical segment;

the second part further having one or more circumferentially oriented beads disposed on the cylindrical exterior surface each bead having a barb-like shape presenting a forward edge which forms an acute angle with said cylindrical exterior surface and a backward edge which is substantially perpendicular to said cylindrical exterior surface; and a roughened surface on the exterior surfaces of the first and second parts;

wherein the bead counter-acts the removal of said cup from the cavity and the toughened surface on the exterior of the first and second parts serves as a file when said cup is moved or rotated in said cavity.

2. A cup according to claim 1 wherein the roughened surface on the exterior surfaces of the first and second parts is produced by the process of blasting the surfaces with particles of $TiO_2$ or of $Al_2O_3$.

3. A cup according to claim 1 wherein the circumferential bead is in the form of at least one thread.

4. A cup according to claim 3, wherein the beads are in the form of one or several series of sections, each section being shorter than the entire circumference of the respective part of the cup.

5. A cup according to claim 4, wherein the sections are separated by gaps extending longitudinally along the axis of the cylindrical part, through the entire beaded part.

* * * * *